United States Patent [19]

DesLauriers et al.

[11] Patent Number: 5,446,227
[45] Date of Patent: Aug. 29, 1995

[54] CO-PRODUCTION OF AN ALKENYL AROMATIC COMPOUND OR PRECURSOR THEREOF AND AN OXYGENATED SULFUR-CONTAINING COMPOUND

[75] Inventors: Paul J. DesLauriers; Michael S. Matson, both of Bartlesville, Okla.

[73] Assignee: Phillips Petroleum Company, Bartlesville, Okla.

[21] Appl. No.: 128,498

[22] Filed: Sep. 7, 1993

[51] Int. Cl.$^6$ .................. C07C 1/00; C07C 315/02
[52] U.S. Cl. .................. 585/437; 585/436; 585/440; 585/441; 568/27; 568/28
[58] Field of Search ............ 585/435, 436, 437, 440, 585/441; 568/27, 28, 32, 34, 35

[56] References Cited

U.S. PATENT DOCUMENTS

| | | | |
|---|---|---|---|
| 3,351,635 | 11/1967 | Kollan | 260/682 |
| 3,459,810 | 8/1969 | Choo et al. | 260/610 |
| 3,658,928 | 4/1972 | Skinner et al. | 260/669 QZ |
| 4,150,059 | 4/1979 | Lamson et al. | 260/650 R |
| 4,233,467 | 11/1980 | Lamson et al. | 585/437 |
| 4,749,674 | 6/1988 | Dejaifve et al. | 502/304 |

FOREIGN PATENT DOCUMENTS 1225167 9/1966 Germany .

OTHER PUBLICATIONS

Kirk–Othmer Encyclopedia of Chemical Technology, vol. 22, pp. 965–973, 1983.
Thiophene and Its Derivatives, Part One, Ed. S. Gronowitz, 1985, pp. 713–715.
J. Chem. Soc. 1950 pt. I, pp. 445–452 (1950).
J. Chem. Soc. 93–T2, pp. 1833–1836 (1908).
CA96:68589m (1982).
World Petroleum Congress/Hydrocarbon Oxidation, vol. 46, pp. 141–143 (Apr. 1967).

*Primary Examiner*—P. Achutamurthy
*Attorney, Agent, or Firm*—Lucas K. Shay

[57] ABSTRACT

A process for co-production of an alkenyl aromatic compound such as, for example, styrene and t-butylstyrene, and an oxygenated sulfur-containing compound such as, for example, a sulfoxide or a sulfone is disclosed which comprises: (1) contacting, in the presence or absence of a catalyst, an α-methyl benzylic hydroperoxide with an organic sulfide compound to produce a mixture of an α-methyl benzylic hydroxide and an oxygenated sulfur-containing compound; (2) separating the α-methyl benzylic hydroxide from the sulfur-containing compound; (3) contacting the α-methyl benzylic hydroxide with a base to convert the α-methyl benzylic hydroxide to the alkenyl aromatic compound; and optionally, (4) recovering the alkenyl aromatic compound from the oxygenated sulfur-containing compound. The sulfoxide produced can be oxidized to a sulfone. The contacting of the α-methyl benzylic hydroxide with a base can also be carried out before the α-methyl benzylic hydroxide is separated from the oxygenated sulfur-containing compound followed by separation of the sulfur-containing compound.

22 Claims, No Drawings

CO-PRODUCTION OF AN ALKENYL AROMATIC COMPOUND OR PRECURSOR THEREOF AND AN OXYGENATED SULFUR-CONTAINING COMPOUND

FIELD OF THE INVENTION

This invention relates to co-production of an alkenyl aromatic compound such as, for example, t-butylstyrene, or precursor, thereof and an oxygenated sulfur-containing compound.

BACKGROUND OF THE INVENTION

An alkenyl aromatic compound such as a styrenic compound is a class of important industrial chemicals. For example, styrene is a starting material for resins, plastics, rubbers, and chemical intermediates. Tert-butylstyrene is useful as comonomer for preparing copolymers, as curing agent for fiber-reinforced plastics, or in improving the moldability of plastics.

It is generally known that these commercially important styrenic compounds are prepared from their corresponding precursors by thermal or catalytic dehydrogenation with steam or oxygen. The processes of dehydrogenation require expensive and sometimes complicated catalysts. Furthermore, the yield and selectivity are generally very low partly because, especially in the case of alkyl-substituted aromatic compound, the dehydrogenation can occur at carbon atoms other than the benzylic carbons. The longer the alkyl substituents, the more severe this problem becomes. Other problems include the use of very expensive starting materials, polymerization of the olefins-containing product mixtures at elevated temperatures, and extreme difficulty in separation of the desired products from undesired products, unreacted reactants and catalysts.

An oxygenated sulfur-containing compound is useful in a variety of industrial applications. For example, sulfolane can be used in pesticidal compositions, intermediates in the production of other organic chemicals, selective solvents to separate aromatic compounds from petroleum fractions, and selective solvents in alkylation of olefins.

Sulfolane-type compounds are generally prepared by catalytic hydrogenation of their corresponding sulfolene compounds. The sulfolene compounds are prepared by the reaction of a conjugated diene such as, for example, 1,3-butadiene, and sulfur dioxide at elevated temperatures.

However, the sulfolene compounds thus-produced are generally unstable and tend to decompose at mildly elevated temperatures into an unsaturated organic compound and sulfur dioxide. Furthermore, when the sulfolene compounds are used to prepare the corresponding sulfolane compounds by catalytic hydrogenation, the initiation of hydrogenation reaction may also increase the temperature enough to result in some decomposition of the sulfolene. Some of these decomposed products polymerize and the resulting polymer coats the hydrogenation catalyst significantly reducing its activity. Moreover, unreacted sulfur dioxide and the sulfur dioxide obtained from decomposition of sulfolene compounds also interfere with the subsequent catalytic hydrogenation. These sulfur dioxides must be removed or substantially reduced.

Another example of oxygenated sulfur-containing compound is bis(4,4′-chlorophenyl) sulfone that can be used as monomer for producing polymers or copolymers of aromatic sulfones. An inexpensive and easy process for producing this sulfur-containing compound has not yet been developed.

Therefore, there is an ever present need to develop more effective methods of producing an alkenyl aromatic compound such as a styrenic compound with concurrent production of an oxygenated sulfur-containing compound.

SUMMARY OF THE INVENTION

An object of the present invention is to provide a process for producing an alkenyl aromatic compound, or precursor thereof. Another object of the invention is to provide a process for producing an oxygenated sulfur-containing compound. A further object of the invention is to provide a process for producing an alkenyl aromatic compound, or precursor thereof, and an oxygenated sulfur-containing compound. An advantage of the present invention is to produce the alkenyl aromatic compound or precursor thereof and oxygenated sulfur-containing compound under mild conditions. Another advantage of the present invention is the co-production of an alkenyl aromatic compound, or precursor thereof, and an oxygenated sulfur-containing compound. Other objects, aspects, features and advantages will become more apparent as the invention is more fully disclosed hereinbelow.

According to the present invention, a process for co-production of an alkenyl aromatic compound, or precursor thereof, and an oxygenated sulfur-containing compound is provided which comprises: (1) contacting an α-methyl benzylic hydroperoxide with an organic sulfide compound to produce a mixture of α-methyl benzylic hydroxide and an oxygenated sulfur-containing compound; (2) separating the α-methyl benzylic hydroxide from the oxygenated sulfur-containing compound; (3) adding a basic compound to the α-methyl benzylic hydroxide to convert the α-methyl benzylic hydroxide to an alkenyl aromatic compound; wherein the oxygenated sulfur-containing compound is selected from the group consisting of a sulfoxide compound, a sulfone compound, and mixtures thereof. Optionally, the sulfoxide compound, if produced, is oxidized to a sulfone compound and the alkenyl aromatic compound and oxygenated sulfur-containing compound are recovered.

DETAILED DESCRIPTION OF THE INVENTION

According to the present invention, the α-methyl benzylic hydroperoxide has the formula of

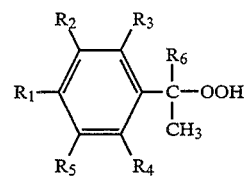

where $R_1$, $R_2$, $R_3$, $R_4$, $R_5$ and $R_6$ can be the same or different and is each selected from the group consisting of hydrogen, hydroxyl, chlorine, bromine, iodine, amine, a hydrocarbyl radical, and mixtures thereof. The hydrocarbyl radical has about 1 to about 10 carbon atoms and is selected from the group consisting of alkyl, alkenyl, aryl, aralkyl, alkaryl, and combinations of two or more thereof. The hydrocarbyl radical can be linear, branched, cyclic, or combinations thereof. Examples of suitable α-methyl benzylic hydroperoxides include, but are not limited to, cumene hydroperoxide, α-methylbenzyl hydroperoxide, p-t-butyl-α-methylbenzyl hydroperoxide, o-t-butyl-α-methylbenzyl hydroperoxide, m-t-butyl-α-methylbenzyl hydroperoxide, p-ethyl-α-methylbenzyl hydroperoxide, p-methyl-α-methylbenzyl hydroperoxide, p-t-butyl-α-methyl-α-propylbenzyl hydroperoxide, p-t-butyl-α-methyl-α-butylbenzyl hydroperoxide, p-ethyl-α-methyl-α-ethylbenzyl hydroperoxide, p-chloro-α-methyl-α-ethylbenzyl hydroperoxide, and combinations thereof. The presently preferred α-methyl benzylic hydroperoxides are α-methylbenzyl hydroperoxide, cumene hydroperoxide, and t-butyl-α-methylbenzyl hydroperoxide because their corresponding alkenyl aromatic products are of importance to industrial applications.

The α-methyl benzylic peroxide can be synthesized by any known processes in the art, such as the process disclosed in U.S. Pat. No. 3,459,810, which is incorporated herein by reference. An example for synthesizing the peroxide is illustrated in Example I.

The term "alkenyl aromatic compound" used herein is referred to, unless otherwise indicated, as a chemical compound having the formula of

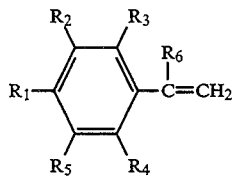

where $R_1$, $R_2$, $R_3$, $R_4$, $R_5$ and $R_6$ are the same as those described above. Suitable alkenyl aromatic compounds include, but are not limited to, styrene, p-t-butylstyrene, α-methyl styrene, p,α-dimethylstyrene, o-t-butylstyrene, p-chlorostyrene, p-ethylstyrene, and combinations thereof. The presently preferred alkenyl aromatic compounds are styrene and t-butylstyrene because of their utility as monomer for polymers and copolymers.

The term "oxygenated sulfur-containing" used in the present invention is referred to as, unless otherwise indicated, a chemical which has a sulfur linkage between two adjacent carbon atoms and the sulfur is oxygenated with 1 to 2 oxygens such as, for example, tetramethylene sulfoxide, and various substituted derivatives thereof. Various organic, inorganic, or both, radicals such as, for example, chlorine, bromine, iodine, alkyl, alkenyl, aryl, aralkyl, alkaryl or combinations thereof, can be substituted for one or more of the hydrogen atoms of the carbon atoms. Total carbon atoms can range from about 2 to about 30, preferably 2 to 20. In general, for example, the tetramethylene sulfoxide compound contain a total of from 4 to about 18 carbon atoms. The presently preferred oxygenated sulfur-containing compounds include, but are not limited to, dimethyl sulfone, diethyl sulfone, diphenyl sulfone, bis(4,4'-chlorophenyl) sulfone, tetramethylene sulfoxide, 2,4-dimethyl tetramethylene sulfoxide, 3,4-epoxy tetramethylene sulfoxide, diphenyl sulfoxide, bis(4,4'-chlorophenyl) sulfoxide, a sulfolane-type compound, and mixtures thereof.

The term "sulfolane-type compound" as employed herein is referred to as tetramethylene sulfone as well as a substituted derivative thereof. The substituent can be an inorganic, an organic, or combinations of both, radicals. Examples of such substituents include, but are not limited to chlorine, bromine, iodine, alkyl, alkenyl, aryl, aralkyl, alkaryl, and combinations thereof. Generally the sulfolane compound contains a total of 4 to 18 carbon atoms. Examples of suitable sulfolane compounds are 2,3,4,5-tetrahydrothiophene-1,1-dioxide (hereinafter referred to as sulfolane), 2,4-dimethyl sulfolane, 3,4-epoxy sulfolane, 3-methyl sulfolane, an ether sulfone having the formula of

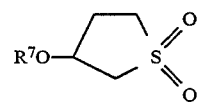

wherein $R_7$ is a $C_1$–$C_{20}$ alkyl group, and combinations thereof.

According to the present invention, the organic sulfide compound can be a dialkyl sulfide, diaryl sulfide, dialkenyl sulfide, alkyl aryl sulfide and mixtures thereof. The sulfide compound can be linear, branched, or cyclic sulfide having about 2 to about 30, preferably 2 to about 18 carbon atoms and various substituted derivatives thereof. Various organic, inorganic, or both, radicals, such as, for example, chlorine, bromine, iodine, alkyl, alkenyl, aryl, aralkyl, alkaryl, or combinations thereof, can be substituted for one or more of the hydrogen atoms of the organic sulfide molecule. Generally, for example, a thiophane compound can contain a total of 4 to about 18 carbon atoms. The presently preferred organic sulfide compounds include, but are not limited to, tetrahydrothiophene (hereinafter referred to as thiophane), 2,4-dimethyl thiophane, 3,4-epoxy thiophane, 3-methyl thiophane, an ether having the formula of

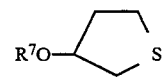

wherein $R^7$ is a $C_1$–$C_{20}$ alkyl groups, bis(4,4'-chlorophenyl) sulfide, tetramethylene sulfide, 2,4-dimethyltetramethylene sulfide, 3,4-epoxytetramethylene sulfide, and combinations thereof.

The molar ratio of the α-methyl benzylic hydroperoxide to the sulfide compound can vary widely depending on the types of the hydroperoxide and the sulfide used in the reaction, and is generally in the range of from about 0.1:1 to 2.0:1, desirably from about 0.5:1 to about 1.5:1, and preferably from 0.8:1 to 1:1. Generally, if a sulfoxide is a desired product, an excess sulfide is preferred and if a sulfone is a desired product, then an excess hydroperoxide is preferred.

According to the present invention, the first step is to contact an α-methyl benzylic hydroperoxide with an organic sulfide compound under conditions sufficient to produce a mixture of an α-methyl benzylic hydroxide and an oxygenated sulfur-containing compound. The contacting can be carried out over a wide range of temperatures from about 10° C. to about 100° C., preferably about 15° C. to about 80° C., and most preferably 20° C. to 50° C. The contacting can also be carried out over a wide pressure range from about 1 atmosphere (atm) to about 70 atm, preferably about 1 atm to about 50 atm, and most preferably 1 atm to 10 atm. The time required for completion of the reaction is generally from about 10 minutes to about 6 hours.

The contacting of the α-methyl benzylic hydroperoxide with the organic sulfide compound can also be carried out in the presence of a catalyst selected from the group consisting of tungstic acid, vanadium, molybdenum, vanadium oxides, molybdenum oxides, naphthenates, and combinations thereof. The presently preferred catalyst is tungstic acid because of its ready availability.

According to the present invention, the contacting of the α-methyl benzylic with the organic sulfide compound can also be carried out in the presence of a solvent to improve the solubility of the reaction medium including, but not limited to, the reactants and catalyst, if present. Examples of suitable solvents are methanol, ethanol, propanol isopropyl alcohol, butanol, pentanol, acetone, methylethyl ketone, tetrahydrofuran, and mixtures thereof. The molar ratio of the solvent to the organic sulfide compound can vary widely depending on the type of reactants and catalyst, if present, employed. In general, the molar ratio is in the range of from about 0.1:1 to about 100:1.

Once the mixture of the α-methyl benzylic hydroxide and the oxygenated sulfur-containing compound is produced, the α-methyl benzylic hydroxide can be separated from the oxygenated sulfur-containing compound. The α-methyl benzylic hydroxide can then be contacted with a basic compound to convert the α-methyl benzylic hydroxide to an alkenyl aromatic compound.

The basic compound useful as a component of the present invention can be an organic or an inorganic base, or mixtures thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, and mixtures of any two or more thereof. Suitable inorganic bases include, but are not limited to, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, RONa, RSNa, and mixtures of any two or more thereof; where R is a $C_1$-$C_{18}$ alkyl radical. Presently, an inorganic base is preferred because of availability and low cost of inorganic bases. Among the inorganic bases, sodium hydroxide and potassium hydroxide are preferred because they are readily available and inexpensive.

The molar ratio of the basic compound to the α-methyl benzylic hydroxide compound is generally in the range of from about 0.0001:1 to about 0.5:1, preferably from about 0.001 to about 0.1, and most preferably from 0.005 to 0.05. The conditions for contacting the basic compound with the α-methyl benzylic hydroxide to convert the α-methyl benzyl hydroxide to its corresponding alkenyl aromatic compound are the same as those disclosed in the first step of the process.

Dehydration of the α-methylbenzylic hydroxide can also be carried out over a titania catalyst at about 200°–250° C. See World Petroleum Congress/Hydrocarbon Oxidation, Vol. 46, pages 141–143 (1967). Alternatively, the conversion of the α-methyl benzylic hydroxide compound to its corresponding alkenyl aromatic compound can be carried out by any known method such as the process disclosed in U.S. Pat. No. 4,150,059, which is incorporated herein by reference.

When substantially all α-methyl benzyl hydroxide is converted to the alkenyl aromatic compound, it generally takes about 10 minutes to about 6 hours to complete the conversion of the α-methyl benzyl hydroxide to the alkenyl aromatic compound. The conversion of the α-methyl benzylic hydroxide can also be monitored by the formation of the alkenyl aromatic compound by methods well known to one skilled in the art such as, for example, high pressure liquid chromatography.

According to the present invention, the mixture containing the α-methyl benzylic hydroxide and the oxygenated sulfur-containing compound can also be contacted with the basic compound to convert the α-methyl benzylic hydroxide to the alkenyl aromatic compound followed by separating the alkenyl aromatic compound from the oxygenated sulfur-containing compound. Separation of the α-methyl benzyl hydroxide or alkenyl aromatic compound from the oxygenated sulfur-containing compound can be carried out by conventional means generally known to one skilled in the art. Examples of suitable separation means include, but are not limited to, crystallization, distillation, solvent extraction, chromatography, and combinations thereof. The presently preferred separation method is distillation.

The production of the alkenyl aromatic compound and oxygenated sulfur-containing compound can be monitored by a variety of means such as, for example, infrared spectroscopy, gas chromatography, liquid chromatography, and combinations thereof. The presently preferred method is high pressure liquid chromatography (HPLC) which is well known to one skilled in the art.

If desired, the sulfoxide compound, if produced by the process of the invention, can be further oxidized to its corresponding sulfone compound by methods well known to those skilled in the art. One of such methods in the oxidation of the sulfoxide with hydrogen peroxide to its corresponding sulfone. Because the oxidation is well known to those skilled in the art such oxidation process is omitted herein in the interest of brevity.

According to the present invention, the alkenyl aromatic compound and the oxygenated sulfur-containing compound can be recovered by many means known to one skilled in the art such as, for example, fractional distillation, solvent extraction, crystallization, chromatography, and combinations thereof. The presently preferred recovery method is fractional distillation.

The following examples are provided to merely illustrate the process of the invention and are not intended to limit the scope of the invention. The percentage data shown in the Examples are weight percent.

EXAMPLE I

This example demonstrates the synthesis of t-butyl-α-methyl benzyl hydroperoxide (TBEB-OOH) from t-butylethylbenzene (TBEB). A 100 g sample of TBEB and 1.5 g of cumene hydroperoxide as catalyst was charged to a three necked 250 mL flask fitted with a magnetic stirring bar, water cooled condenser, and sparging tube. The reaction mixture was heated to 125° C. with stirring using a heating mantal and stirring plate. Oxygen was then bubbled in at the rate of 7 liters per hour for 6 h. A subsequent titration of the resulting yellow reaction solution showed that 18.84 wt % TBEB-OOH was produced.

EXAMPLE II

This example illustrates the general procedure for carrying out the present invention. A 2.511 g sample of a 16.68 wt % (2.16 mmol) p-t-butyl-α-methylbenzyl hydroperoxide (TBEB-OOH) in p-t-butyl ethylbenzene (TBEB) solution was added to a 21×7 mm 4 dram vial equipped with a stirring bar. Excess thiophane (0.437 g; 4.96 mmol) was then added to the reaction mixture. The reaction mixture was stirred at room temperature for 3 h. Reaction temperature was controlled by placing the vial in an aluminum block mounted on a hot plate/stirrer apparatus. A thermometer immersed in a vial containing 99% pure p-t-butyl ethylbenzene (2 mL) was placed in the center hole of the aluminum block and used to monitor reaction temperature. After the allotted reaction time the mixture was analyzed for its contents using HPLC and GC.

Analyses of the resulting reaction mixture by HPLC showed that thiophane reacted with the hydroperoxide to produce the alkenyl aromatic compound precursor, (i.e., TBEB-OH). Tetramethylene sulfoxide was the main oxidized product obtained in this reaction as detected by gas chromatography (GC) analysis. Table I lists the percent yields for the resulting products. These results clearly demonstrate the co-production of the alkenyl aromatic compound precursor, (i.e., TBEB-OH) and oxidized sulfur-containing products.

TABLE I

| Reaction of Excess Thiophane with TBEB-OOH | | | |
|---|---|---|---|
| % Remaining TBEB-OOH | % Yield[a] TBEB-OH | % Yield[b] Sulfoxide | % Yield[b] Sulfone |
| 5.66 (0.12 mmol) | 78.6 (1.60 mmol) | ~100.0 (1.73 mmol) | trace |

[a]Based on thiophane limiting reagent; within 9% error using 99% pure TBEB-OH as standard in HPLC analysis.
[b]Based on thiophane as limiting reagent; within 6% error using commercial tetramethylene sulfoxide as standard in GC analysis.

EXAMPLE III

This example illustrates the reaction of thiophane with a slight excess of p-t-butyl-α-methylbenzyl hydroperoxide (TBEB-OOH). Thiophane (0.15 mL; 1.72 mmol) was added to ~2 mL (1.96 g) of 17.87 wt % TBEB-OOH (1.80 mmol) in p-t-butyl ethylbenzene (TBEB). The reaction was carried out at 80° C. for 3 hours using those methods described in Example II.

Analyses of the resulting reaction mixture by HPLC and GC showed that both starting materials were consumed (Table I). Also given in Table II are the percent yields for the resulting products. These results clearly demonstrate the co-production of the alkenyl aromatic compound precursor, (i.e. p-t-butyl-α-methylbenzyl alcohol; TBEB-OH) and oxidized sulfur-containing products.

TABLE II

| Reaction of Slight Excess TBEB-OOH with Thiophane | | | | | |
|---|---|---|---|---|---|
| Run | % Remaining TBEB-OOH | % Remaining Thiophane | % Yield[a] TBEB-OH | % Yield[b] Sulfoxide | % Yield[b] Sulfone |
| 1 | trace | 0.0 | 68.6 (1.18 mmol) | ~100.0 (1.74 mmol) | trace |
| 2 | trace | 0.0 | 65.8 (1.13 mmol) | 97.2 (1.67 mmol) | trace |

[a]Based on thiophane as limiting reagent; within 9% error using 99% pure TBEB-OH as standard in HPLC analysis.
[b]Based on thiophane as limiting reagent; within 6% error using commercial tetramethylene sulfoxide as standard in GC analysis.

EXAMPLE IV

This example illustrates how the product ratio of oxidized sulfur products will vary when thiophane is reacted with cumene hydroperoxide in the presence of a solvent (isopropyl alcohol) and a tungstic acid catalyst. Thiophane (0.05 mL; 0.57 mmol) was added to a vial containing 2.0 g of 18.22 wt % cumene hydroperoxide (COOH; 0.86 mmol) in cumene, isopropyl alcohol (1.0 g), and tungstic acid (0.021 g; 0.084 mmol). The reaction was carried out at 70° C. for 3 hours using the method described in Example II.

Analyses of the resulting reaction mixtures by GC shown in Table III, illustrated that under these conditions the sulfoxide to sulfone ratio was substantially changed from that found in Examples II and III.

TABLE III

| Reaction of Excess Cumene Hydroperoxide with Thiophane in Isopropyl Alcohol Using a Tungstic Acid Catalyst | | | | |
|---|---|---|---|---|
| Run | % Remaining Thiophane | Sulfoxide[a] (mmol) | Sulfone[b] (mmol) | Sulfoxide/ Sulfone |
| 1 | 0.0 | 0.21 | 0.64 | 1:3.1 |
| 2 | 0.0 | 0.35 | 0.56 | 1:1.6 |

[a]Within 6% error using commercial tetramethylene sulfoxide as standard in GC analysis.
[b]Calculated from ratio of molecular weight adjusted peak areas in GC.

The results shown in the above sample clearly demonstrate that the present invention is well adapted to carry out the objects and attain the end and advantages mentioned as well as those inherent therein. While modifications may be made by those skilled in the art, such modifications are encompassed within the spirit of the present invention as defined by the specification and the claims.

That which is claimed is:

1. A process for producing an alkenyl aromatic compound, or precursor thereof, and an oxygenated sulfur-containing compound comprising:

(1) contacting an α-methyl benzylic hydroperoxide with an organic sulfide under conditions sufficient to produce a mixture of an α-methyl benzylic hydroxide which is a precursor of said alkenyl aromatic compound, and said oxygenated sulfur-containing compound;

(2) separating said α-methyl benzylic hydroxide from said oxygenated sulfur-containing compound; and (3) contacting said α-methyl benzylic hydroxide with a basic compound to convert said α-methyl benzylic hydroxide to an alkenyl aromatic compound; wherein said oxygenated sulfur-containing compound is selected from the group consisting of a sulfoxide, a sulfone, and mixtures thereof; said organic sulfide is selected from the group consisting of thiophase, 2,4-dimethyl thiophane, 3,4-epoxy thiophane, 3-methyl thiophane, an ether having the formula of

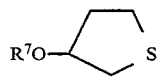

in which $R^7$ is a $C_1$–$C_{20}$ alkyl radical, and combinations thereof; and said basic compound is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, RONa, RSNa, and mixtures of any two or more thereof: wherein R is a $C_1$–$C_{18}$ alkyl radical.

2. A process according to claim 1 further comprising contacting said sulfoxide with an oxidizing agent selected from the group consisting of tungstic acid, vanadium, molybdenum, vanadium oxides, molybdenum oxides, and combinations thereof.

3. A process according to claim 1 further comprising recovering said alkenyl aromatic compound and said oxygenated sulfur-containing compound.

4. A process according to claim 1 wherein said alkenyl aromatic compound has the formula of

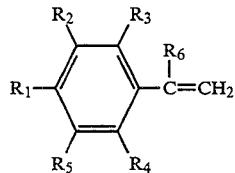

wherein $R_1$, $R_2$, $R_3$, $R_4$, $R_5$ and $R_6$ can be the same or different and is each selected from the group consisting of hydrogen, hydroxyl, chlorine, bromine, iodine, amine, a hydrocarbyl radical, and mixtures thereof; wherein said hydrocarbyl radical has about 1 to about 10 carbon atoms and is selected from the group consisting of alkyl, alkenyl, aryl, aralkyl, alkaryl, and combinations thereof.

5. A process according to claim 4 wherein said alkenyl aromatic compound is selected from the group consisting of styrene, t-butylstyrene, and mixtures thereof.

6. A process according to claim 1 wherein said oxygenated sulfur-containing compound is selected from the group consisting of tetramethylene sulfoxide, sulfolane and mixtures thereof.

7. A process according to claim 1 wherein said α-methyl benzylic hydroperoxide has the formula of

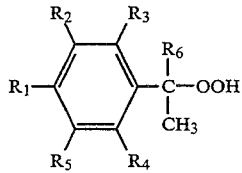

wherein $R_1$, $R_2$, $R_3$, $R_4$, $R_5$ and $R_6$ can be the same or different and is each selected from the group consisting of hydrogen, hydroxyl, chlorine, bromine, iodine, amine, a hydrocarbyl radical, and mixtures thereof; wherein said hydrocarbyl radical has about 1 to about 10 carbon atoms and is selected from the group consisting of alkyl, alkenyl, aryl, aralkyl, alkaryl, and combinations thereof.

8. A process according to claim 7 wherein said α-methyl benzylic hydroperoxide is selected from the group consisting of cumene hydroperoxide, α-methylbenzyl hydroperoxide, p-t-butyl-α-methylbenzyl hydroperoxide, o-t-butyl-α-methylbenzyl hydroperoxide, m-t-butyl-α-methylbenzyl hydroperoxide, p-ethyl-α-methylbenzyl hydroperoxide, p-methyl-α-methylbenzyl hydroperoxide, p-t-butyl-α-methyl-α-propylbenzyl hydroperoxide, p-t-butyl-α-methyl-α-butylbenzyl hydroperoxide, p-ethyl-α-methyl-α-ethylbenzyl hydroperoxide, p-chloro-α-methyl-α-ethylbenzyl hydroperoxide, and combinations thereof.

9. A process according to claim 8 wherein said α-methyl benzylic hydroperoxide is selected from the group consisting of cumene hydroperoxide, α-methylbenzyl hydroperoxide, p-t-butyl-α-methylbenzyl hydroperoxide, and mixtures thereof.

10. A process according to claim 1 wherein said organic sulfide is thiophane.

11. A process according claim 1 wherein step (1) is conducted in the presence of a catalyst.

12. A process according to claim 11 wherein said catalyst is selected from the group consisting of tungstic acid, vanadium, molybdenum, vanadium oxides, molybdenum oxides, and combinations thereof.

13. A process according to claim 12 wherein said catalyst is tungstic acid.

14. A process according to claim 1 wherein said basic compound is selected from the group consisting of sodium hydroxide, potassium hydroxide, and combinations thereof.

15. A process according to claim 1 wherein step (1) is carried out at a temperature in the range of about 10° C. to about 100° C.

16. A process according to claim 15 wherein said temperature is in the range of 20° C. to 50° C.

17. A process according to claim 1 wherein said process comprises:

(1) contacting, at about 15° C. to about 80° C., α-methylbenzyl hydroperoxide, p-t-butyl-α-methylbenzyl hydroperoxide, or mixtures thereof, with thiophane to produce, respectively, α-methylbenzyl hydroxide, p-t-butyl-α-methylbenzyl hydroxide, or mixtures thereof; and an oxygenated sulfur-containing compound, which comprises tetramethylene sulfoxide and sulfolane;

(2) separating said α-methylbenzyl hydroxide and/or p-t-butyl-α-methylbenzyl hydroxide from said oxygenated sulfur-containing compound;

(3) contacting said α-methyl benzylic hydroxide with potassium hydroxide to produce an alkenyl aromatic compound, which comprises styrene and/or p-t-butylstyrene; and (4) recovering said oxygenated sulfur-containing compound from said alkenyl aromatic compound.

18. A process according to claim 1 wherein step (1) is carried out in a solvent.

19. A process for producing p-t-butylstyrene and tetramethylene sulfoxide comprising contacting, at 20° C. to 50° C., p-t-butyl-α-methylbenzyl hydroperoxide with thiophane to produce a mixture of p-t-butyl-α-methyl benzyl hydroxide and tetramethylene sulfoxide followed by contacting said p-t-butyl-α-methyl benzyl hydroxide with potassium hydroxide to convert said p-t-butyl-α-methyl benzyl hydroxide to said p-t-butylstyrene.

20. A process for producing styrene, tetramethylene sulfoxide and sulfolane comprising contacting, at 20° C. to 50° C., α-ethylbenzyl hydroperoxide with thiophane to produce a mixture of α-methylbenzyl hydroxide, tetramethylene sulfoxide and sulfolane followed by contacting said α-methylbenzyl hydroxide with potassium hydroxide to convert said α-methylbenzyl hydroxide to styrene.

21. A process for producing an alkenyl aromatic compound and an oxygenated sulfur-containing compound comprising: (1) contacting an α-methyl benzylic hydroperoxide with an organic sulfide under conditions sufficient to produce a mixture of an α-methyl benzylic hydroxide and said oxygenated sulfur-containing compound; (2) contacting said mixture with NaOH or KOH under conditions sufficient to convert said α-methyl benzylic hydroxide to an alkenyl aromatic compound; and (3) separating said oxygenated sulfur-containing compound from said alkenyl aromatic compound; wherein said oxygenated sulfur-containing compound is selected from the group consisting of a sulfoxide, a sulfone, and mixtures thereof.

22. A process according to claim 1 wherein said organic sulfide is a substituted organic sulfide.

* * * * *